United States Patent
Guram et al.

(10) Patent No.: US 6,350,916 B1
(45) Date of Patent: Feb. 26, 2002

(54) SELECTIVE OXIDATION OF ALCOHOLS TO ALDEHYDES OR KETONES

(75) Inventors: Anil Guram, San Jose; Xiaohong Bei, Santa Clara, both of CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/531,855

(22) Filed: Mar. 21, 2000

Related U.S. Application Data

(63) Continuation-in-part of application No. 09/252,182, filed on Feb. 18, 1999, which is a continuation-in-part of application No. 09/062,128, filed on Apr. 17, 1998.
(60) Provisional application No. 60/095,612, filed on Aug. 6, 1998.

(51) Int. Cl.$^7$ .............................................. C07C 45/29
(52) U.S. Cl. ........................ 568/320; 568/357; 568/399; 568/471
(58) Field of Search ................................ 568/309, 322, 568/323, 338, 361, 364, 403, 407, 437, 443, 449, 485, 490, 814, 880, 881, 320, 357, 399, 471

(56) References Cited

FOREIGN PATENT DOCUMENTS

WO    WO 00/08032    2/2000

OTHER PUBLICATIONS

Tamaru, Y. et al., "Oxidation of Primary and Secondary Alcohols by the Catalysis of Palladium," *J. Org. Chem.* 1983, 48, pp. 1286–1292.

Tamaru, Y., et al., "Palladium Catalyzed Oxidations of Secondary Alcohols," *Tet. Lett.* 1979, 16, pp. 1401–1404.

Nagashima, H., et al., "Activation of Polyhaloalkanes by Palladium Catalyst: Palladium Catalyzed Oxidation of Alcohols to Carbonyl Compounds with Carbon Tetrachloride," *Chem. Lett.* 1981, pp. 1171–1172.

Tsuji, J. et al., "A Palladium Catalyzed Conversion of Halohydrins to Ketones," *Tet. Lett.* 1982, pp. 3085–3088.

Bouquillon, S., et al., "Critical Role of the Coordination Environment of Palladium Dichloride on the Course of Its Reaction with Secondary Benzylic Alcohols: Selective Oxidation or Etherification Catalysts," *Organometallics* 2000, web edition released Mar. 8, 2000.

Mann, G., et al., "Palladium–Catalyzed C–O Coupling Involving Unactivagted Aryl Halides: Sterically Induced Reductive Elimination To Form the C–O Bond in Diaryl Ethers," *J. Am. Chem. Soc.*, 1999, 121, pp. 3224–3225.

Aranyos, A., et al., "Novel Electron–Rich Bulky Phosphine Ligands Facilitate the Palladium–Catalyzed Preparation of Diaryl Ethers," *J. Am. Chem. Soc.*, 1999, 121, pp. 4369–4378.

Mann, G., et al., "Palladium Alkoxides: Potential Intermediacy in Catalytic Amination, Reductive Elimination of Ethers, and Catalytic Etheration. Comment son Alcohol Elimination from Ir(III)," *J. Am. Chem. Soc.*, 1996, 118, pp. 13109–13110.

Goetz, H., et al., *Liebigs Ann. Chem.* (1977), No. 4, pp. 556–564.

Mann, G., et al., "Nickel–vs Palladium–Catalyzed Synthesis of Protected Phenols from Aryl Halides," *J. Org. Chem.*, 1997, 62, pp. 54–13–5418.

Palucki, M., et al., "Synthesis of Oxygen Heterocycles via a Palladium–Catalyzed C—O Bond–Forming Reaction," *J. Am. Chem. Soc.*, 1996, 118, pp. 10333–10334.

Palucki, M., et al., "Palladium–Catalyzed α–Arylation of Ketones," *J. Am. Chem. Soc.*, 1997, 119, pp. 11108–11109.

Mann, G., et al., "Palladium–Catalyzed Formation of Diaryl Ethers from Aryl Bromides. Electron Poor Phosphines Enhance Reaction Yields," *Tetrahedron Letters*, vol. 38, No. 46, pp. 8005–8008, 1997.

Hamachi, K., et al., "Asymmetric Benzylic Oxidation Using a Mn–Salen Complex as Catalyst," *Tetrahedron Letters*, vol. 37, No. 28, pp. 4979–4982, 1996.

Grushin, Vladimir V., et al., "Transformations of Cholorarenes, Catalyzed by Transition–Metal Complexes," *Chemical Reviews* 94(1–4): 1047–1062 (1994).

Pine, Stanley H., "The Variables in Nucleophilic Substitution," p. 329, in *Organic Chemistry* McGraw–Hill, Inc. (1987).

*Primary Examiner*—Sreeni Padmanabhan

(57) ABSTRACT

Alcohols are oxidized to their corresponding ketone or aldehyde using an aryl chloride oxidant and a metal-ligand complex or metal/ligand composition. This reaction is particularly applicable to aromatic alcohols and cyclic and bicyclic aliphatic alcohols.

20 Claims, No Drawings

SELECTIVE OXIDATION OF ALCOHOLS TO ALDEHYDES OR KETONES

This application is a continuation-in-part of U.S. patent application Ser. No. 09/252,182, filed Feb. 18, 1999, which is a continuation-in-part of Ser. No. 09/062128 filed Apr. 17, 1998 and claims benefit of Ser. No. 60/095612 filed Aug. 6, 1998 which is incorporated herein by reference for all purposes.

FIELD OF THE INVENTION

The present invention relates to a process for the selective oxidation of alcohols to aldehydes or ketones by using an aryl chloride, e.g., chlorobenzene, as an oxidant. The process involves reacting a mixture of the alcohol, aryl chloride, and a base in the presence of metal-ligand complex or composition as a catalyst.

BACKGROUND OF THE INVENTION

Ancillary (or spectator) ligand-metal coordination complexes (e.g. organometallic complexes) and compositions are useful as catalysts, additives, stoichiometric reagents, monomers, solid state precursors, therapeutic reagents and drugs. Certain known ancillary ligand-metal complexes and compositions are catalysts for reactions such as oxidation, reduction, hydrogenation, and other transformations. Metal-ligand composition or complex catalyzed selective oxidations of alcohols to aldehydes and ketones typically involve an oxygen atom containing oxidant, e.g., air, oxygen and hydrogen peroxide based oxidations.

Other oxidations of alcohols to ketones or aldehydes based on non-oxygen atom containing oxidants are relatively rare. Examples include oxidations based on aryl bromides (see, e.g., Tamaru, Y. et al., "Oxidation of Primary and Secondary Alcohols by the Catalysis of Palladium," *J. Org. Chem.* 1983, 48, pp. 1286–1292 and Tamaru, Y., et al., "Palladium Catalyzed Oxidations of Secondary Alcohols," *Tet. Lett.* 1979, 16, pp. 1401–1404) and aliphatic chlorides (see, e.g., Nagashima, H., et al., "Activation of Polyhaloalkanes by Palladium Catalyst: Palladium Catalyzed Oxidation of Alcohols to Carbonyl Compounds with Carbon Tetrachloride," *Chem. Lett.* 1981, pp. 1171–1172; Tsuji, J. et al., "A Palladium Catalyzed Conversion of Halohydrins to Ketones," *Tet. Lett.* 1982, pp. 3085–3088; and Bouquillon, S., et al., "Critical Role of the Coordination Environment of Palladium Dichloride on the Course of Its Reaction with Secondary Benzylic Alcohols: Selective Oxidation or Etherification Catalysts," Organometallics 2000, web edition released Mar. 8, 2000). However, these oxidations based on non-oxygen atom containing oxidants are industrially less attractive due to the high cost of aryl bromide and aliphatic chloride oxidants and/or industrially incompatible or unfavorable reaction conditions.

Others have studied a related reaction that forms an ether. The predominant formation of aryl ether products has been previously described to be favored under similar reaction conditions. See, e.g., Mann, G., et al., "Palladium-Catalyzed C—O Coupling Involving Unactivagted Aryl Halides: Sterically Induced Reductive Elimination To Form the C—O Bond in Diaryl Ethers," *J. Am. Chem. Soc.*, 1999, 121, pp. 3224–3225 and Aranyos, A., et al., "Novel Electron-Rich Bulky Phosphine Ligands Facilitate the Palladium-Catalyzed Preparation of Diaryl Ethers," *J. Am. Chem. Soc.*, 1999, 121, pp. 4369–4378.

Despite these attempts, the oxidation of alcohols to the corresponding aldehydes and ketones remains one of the most fundamental and important processes in organic synthesis that has not achieved very economical and environmental conditions. These oxidations are common reactions that are used to make many types of pharmaceuticals. Thus, those of skill in the art have long desired to replace the known processes with a process that does not require the use of expensive raw materials or processes that use environmentally hazardous heavy metals in stoichiometric or excess amounts.

SUMMARY OF THE INVENTION

This invention, then, overcomes at least some of the problems associated with the commercial oxidation of alcohols to the corresponding ketones or aldehydes. The present invention is directed toward the use of aryl chloride oxidants (such as chlorobenzene), which are relatively inexpensive and often used as solvent in industrial processes. This invention offers the additional benefit of allowing the starting alcohol substrate to contain other functionalities (such as sulfur or double or triple bonds) that do not oxidize under the reaction conditions employed. Moreover, the reactions of the present invention are performed at lower pressures than traditional oxidations, since the oxidant is typically in liquid form.

The present invention offers a process for the selective oxidation of alcohols to useful aldehydes and ketones by reacting a mixture of an alcohol, aryl chloride and a base in the presence of metal-ligand complex or composition as a catalyst and a suitable solvent. The products are the corresponding ketone or aldehyde of the starting alcohol substrate and benzene or benzene derivative of the aryl chloride. The invention identifies process conditions, which surprisingly result in the selective and predominant formation of aldehyde and ketone products rather than aryl ether products.

Thus, it is an object of this invention to provide a process for the oxidation of alcohols to ketones or aldehydes using aryl chloride.

It is another object of this invention to provide a process for the selective oxidation of alcohols to ketones or aldehydes where the alcohol comprises other reactive functionalities.

It is a further object of this invention to oxidize alcohols to ketones or aldehydes at lower reaction pressures.

It is yet a further object of this invention to oxidize alcohols to ketones or aldehydes at economically and/or environmentally sound conditions.

These and other objects of the invention are accomplished through a reaction using suitable metal-ligand compositions or complexes that can be generated in situ or separately by adding suitable ligands to suitable precursor metals. Suitable ligands of this process can be characterized by the general formulas $PR_3$, $NR_3$, $SR_2$, $OR_2$, or $:CR_2$ (carbenes) wherein each R is independently selected from the group consisting of hydrocarbyl (e.g., alkyl, alkenyl, alkynyl, aryl, alkaryl, aralkyl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.). Suitable precursor metal complexes can be characterized by the form $ML_n$ wherein M is a transition metal, preferably Pd, Ni, Ru, Rh, Co, Ir, and most preferably Pd and Ni and L is a suitable neutral or charged organic or inorganic fragment or solid support. Suitable bases of this process can be organic and inorganic compounds such as amines, alkali and alkaline earth metal carbonates, phosphates, alkoxides, hydroxides and fluorides. Suitable solvents include hydrocarbons, ethers, ketones, alcohols, and nitriles. Optionally the starting alcohol substrate could be used as the solvent.

Further aspects of this invention will be evident to those of skill in the art upon review of this specification.

DETAILED DESCRIPTION OF THE INVENTION

It is to be understood that unless otherwise indicated this invention is not limited to specific reactants, catalyst compositions (including heteroatom-containing activators and acids), or synthetic methods. It is also to be understood that the terminology used herein is for the purpose of describing particular embodiments only, and is not intended to be limiting.

As used in this specification and the appended claims, the singular forms "a," "an" and "the" include plural referents unless the context clearly dictates otherwise. Thus, reference to "a reagent" includes mixtures of reagents, "a base" includes mixtures of bases, "a catalyst composition" includes mixtures of catalyst compositions, and the like.

In describing and claiming the present invention, the following terminology will be used in accordance with the definitions set out below. A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The following definitions pertain to chemical structures, molecular segments and substituents:

As used herein, the phrase "having the structure" is not intended to be limiting and is used in the same way that the term "comprising" is commonly used. The term "independently selected from the group consisting of" is used herein to indicate that the recited elements, e.g., R groups or the like, can be identical or different (e.g., $R^1$ and $R^2$ in the structure of formula (I) may all be substituted alkyl groups, or $R^1$ may be hydrido and $R^2$ may be methyl, etc.).

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom.

The term "alkenyl" as used herein refers to a branched or unbranched hydrocarbon group typically although not necessarily containing 2 to about 24 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, preferably two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 24 carbon atoms and at least one triple bond, such as ethynyl, n-propynyl, isopropynyl, n-butynyl, isobutynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing one to six, more preferably one to four, carbon atoms. The term "aryloxy" is used in a similar fashion, with aryl as defined below.

Similarly, the term "alkyl thio" as used herein intends an alkyl group bound through a single, terminal thioether linkage; that is, an "alkyl thio" group may be represented as —S-alkyl where alkyl is as defined above. A "lower alkyl thio" group intends an alkyl thio group containing one to six, more preferably one to four, carbon atoms.

The term "allenyl" is used herein in the conventional sense to refer to a molecular segment having the structure —CH═C═CH$_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. In particular embodiments, aryl substituents have 1 to about 200 carbon atoms, typically 1 to about 50 carbon atoms, and preferably 1 to about 20 carbon atoms. "Substituted aryl" refers to an aryl moiety substituted with one or more substituent groups, and the terms "heteroatom-containing aryl" and "heteroaryl" refer to aryl in which at least one carbon atom is replaced with a heteroatom.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. The term "hydrocarbyline" intends a trivalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. Thus, a "hydrocarbyline" may include a "hydrocarbylene." "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom.

By "substituted" as in "substituted hydrocarbyl," "substituted hydrocarbylene," "substituted alkyl," "substituted alkenyl" and the like, as alluded to in some of the aforementioned definitions, is meant that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, phosphino, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

As used herein the term "silyl" refers to the $-SiZ^1Z^2Z^3$ radical, where each of $Z^1$, $Z^2$, and $Z^3$ is independently selected from the group consisting of hydrido and optionally substituted alkyl, alkenyl, alkynyl, aryl, aralkyl, alkaryl, heterocyclic, alkoxy, aryloxy and amino.

As used herein, the term "phosphino" refers to the group $-PZ^1Z^2$, where each of $Z^1$ and $Z^2$ is independently selected from the group consisting of hydrido and optionally substituted alkyl, alkenyl, alkynyl, aryl, aralkyl, alkaryl, heterocyclic and amino.

The term "amino" is used herein to refer to the group $-NZ^1Z^2$, where each of $Z^1$ and $Z^2$ is independently selected from the group consisting of hydrido and optionally substituted alkyl, alkenyl, alkynyl, aryl, aralkyl, alkaryl and heterocyclic.

The term "thio" is used herein to refer to the group $-SZ^1$, where $Z^1$ is selected from the group consisting of hydrido and optionally substituted alkyl, alkenyl, alkynyl, aryl, aralkyl, alkaryl and heterocyclic.

The term "chiral" refers to a structure that does not have an improper rotation axis ($S_n$), i.e., it belongs to point group $C_n$, or $D_n$. Such molecules are thus chiral with respect to an axis, plane or center of asymmetry. Preferred "chiral" molecules herein are in enantiomerically pure form, such that a particular chiral molecule represents at least about 95 wt. % of the composition in which it is contained, more preferably at least about 99 wt. % of that composition.

The term "enantioselective" refers to a chemical reaction that preferentially results in the formation of one enantiomer relative to a second enantiomer, i.e., gives rise to a product mixture in which a desired enantiomer increases in percentage (ratio, weight, mole or volume) over the undesired enantiomer. Thus, a reaction that results in the disappearance of one enantiomer will increase the percentage of the other enantiomer in the product mixture.

The term "substrate" refers generally to a reactant, e.g., the "alcohol" herein. Additional abbreviations used herein include "Cy" to refer to a cyclohexyl group (and thus, "$Cy_2$" refers to two cyclohexyl groups, etc.).

As used herein all reference to the elements and groups of the Periodic Table of the Elements is to the version of the table published by the Handbook of Chemistry and Physics, CRC Press, 1995, which sets forth the new IUPAC system for numbering groups.

In one embodiment, then, the reaction of this invention is believed to proceed by Scheme 1, shown below:

Scheme 1

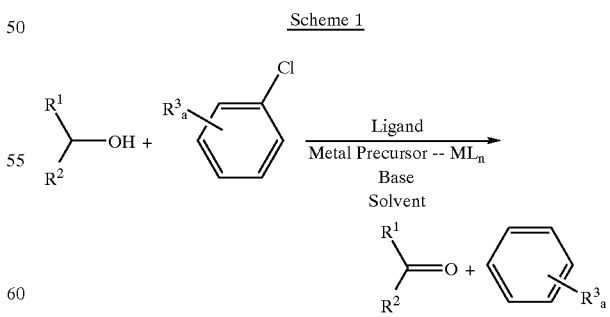

Substrates

The starting alcohol substrate for the process, as shown in Scheme 1, may be characterized by the general formula (I): $R^1R^2CHOH$, where $R^1$ is selected from the group consisting of hydrido, hydroxyl, sulfhydryl, amino, substituted amino, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.), substituted heteroatom-containing hydrocarbyl (e.g., substituted heteroatom-containing alkyl, alkenyl, alkynyl, aryl, aralkyl, alkaryl, etc.), silyl, cyano, boryl, thio and phosphino. $R^2$ is selected from the same group as $R^1$, however, $R^2$ cannot be hydrido when $R^1$ is hydrido. In addition, $R^1$ and $R^2$ may be joined together in a ring structure, including single rings, bicyclic rings and multi-ring structures, where the ring includes the CH portion of the formula. Without wishing to be bound by any particular theory or mechanism, and as discussed below, the $R^1$ and $R^2$ groups are typically chosen so that the hydrogen on the carbon atom that is bound to the alcohol group being oxidized can undergo beta-hydride elimination. Embodiments of this invention that are not preferred are those where the alcohol substrate comprises from 2–4 carbon atoms, for example where $R^1$ is a $C_1$–$C_3$ alkyl and $R^2$ is hydrido or for example where the alcohol is 2-propanol or 2-butanol.

Specific embodiments within the scope of formula I, include:

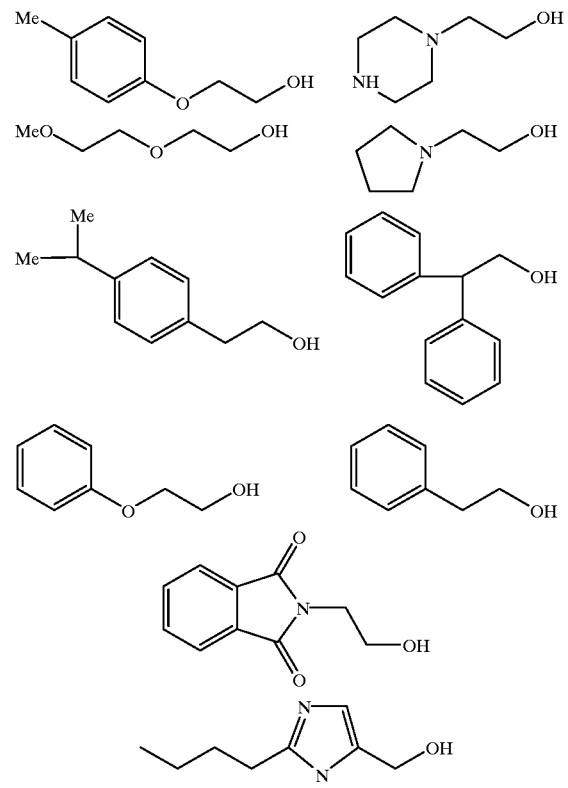

In one preferred embodiment, the starting alcohol substrate includes at least one aryl or other aromatic group as part of either or both $R^1$ and/or $R^2$. Here, the preferred alcohol substrates may be represented by the general formula:

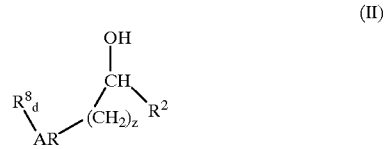

where $R^2$ is as defined above, AR is selected from the group consisting of aryl, cyclopentadienyl, heteroatom-containing aryl and heteroatom-containing cyclopentadienyl; z is 0, 1, 2, 3 or 4; and $R^8$ is selected from the group consisting of hydrido, hydroxyl, sulfhydryl, amino, substituted amino, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.), substituted heteroatom-containing hydrocarbyl (e.g., substituted heteroatom-containing alkyl, alkenyl, alkynyl, aryl, aralkyl, alkaryl, etc.), silyl, cyano, boryl, thio and phosphino and combinations thereof; and d is an integer that reflects the number of substituent $R^8$ groups on the AR, which depends on the chosen AR group. In general, d is 0, 1, 2, 3, 4 or 5. Optionally two or more $R^8$ groups are joined together in a ring structure. Additionally optionally, one or more $R^8$ groups are joined in a ring structure with $R^2$ and/or the aryl to which $R^8$ is attached. Thus, for example, structures such as the following are intended to be included within this preferred embodiment:

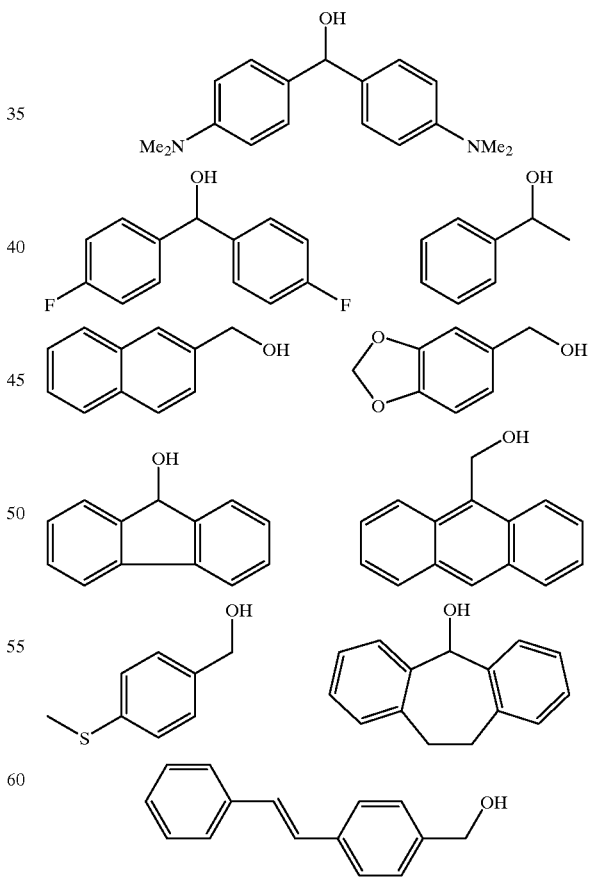

In another preferred embodiment, the starting alcohol substrate is aliphatic, and even more preferably a cyclic or bicyclic aliphatic alcohol. Within this preferred embodiment, the alcohol substrate, when cyclic or bicyclic are 3–15 member rings, which are represented by the general formula:

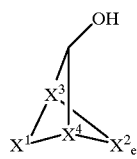

(III)

where $X^1$, $X^2_e$, $X^3$ and $X^4$ are independently a moiety that contains up to 50 atoms. $X^1$ and $X^2$ are typically selected from the group consisting of hydrocarbylene, substituted hydrocarbylene, heteroatom-containing hydrocarbylene and substituted heteroatom-containing hydrocarbylene; and e is 0 or 1. When e is 0, $X^3$ and $X^4$ are selected from the same group as $X^1$. When e is 1, $X^3$ and $X^4$ are selected from the group consisting of hydrocarbyline and substititued hydrocarbyline. $X^1$, $X^2$, $X^3$ and $X^4$ are chosen so that a cyclic or bicyclic alcohol is created. Thus, when a cyclic alcohol is intended, $X^2$ is not present (i.e., e is 0). When a bicyclic alcohol is intended $X^2$ is present (i.e., e is 1). In some preferred embodiments $X^1$ and $X^2$ are selected from the group consisting of lower hydrocarbylene and substituted lower hydrocarbylene, and each independently even more preferably containing from 1–3 carbon atoms. In some preferred embodiments, $X^3$ and $X^4$ are selected from the group consisting of lower hydrocarbyline and substituted lower hydrocarbyline, and each independently even more preferably containing from 2–5 carbon atoms. As discussed above in the definition section, the $X^1$, $X^2$, $X^3$ and $X^4$ may or may not be substituted and may or may not contain heteroatoms. Therefore, one specific bicyclic embodiment is where $X^1$ is ethenyl, $X^2$ is propenyl, $X^3$ is ethyl and $X^4$ is ethyl (which gives the first structure shown below). Another, specific bicyclic embodiment is where $X^1$ is dimethylmethyl, $X^2$ is propenyl, $X^3$ is ethyl and $X^4$ is ethenyl (which gives the second structure shown below), such that alcohols such as the following are included:

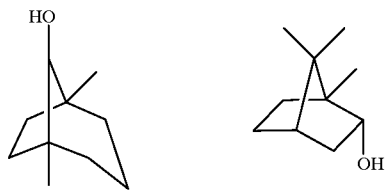

Also, it should be noted that starting alcohol substrates may comprise two or more alcohol groups, each of which may be oxidized into the corresponding ketone or aldehyde or otherwise oxidized.

Aryl Chloride

The aryl chlorides useful in the process of the invention may characterized by the general formula:

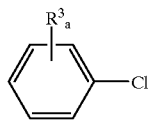

(IV)

where $R^3$ is selected from the group consisting of hydrido, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.), silyl, boryl, phosphino, amino, thio, seleno, and combinations thereof, and a is 0, 1, 2, 3, 4 or 5. Optionally two or more $R^3$ groups are joined together in a ring structure. Preferable, $R^3$ is selected from the group consisting of hydrogen, methyl, ethyl, tert-butyl, methoxy, —CN and —CF$_3$. Also, preferably, a is 0, 1, 2 or 3.

The use of an aryl chloride as just described is considered important to the commercial applicability of this invention. Although others have investigated the use of aryl bromides, those starting materials are expensive and the reactions do not proceed under commercially favorable conditions.

Ligands

The ligands useful in this invention can be characterized by the general formula PR$_3$, where each R is independently selected from the group consisting of hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.). Other ligands that are useful in this invention are other basic ligands (as opposed to non-basic or electron poor ligands), including carbenes that can be characterized by the formula :CR$_2$, where each R is as defined above. Also useful in this invention are ligands such as NR$_3$ and OR$_2$ where each R is as defined above. In preferred embodiments, one or more R groups in the above formulas is independently selected from the group consisting of alkyl and substituted alkyl, with cycloalkyl and substituted cycloalkyl being preferred for at least one R group. Generally, all of the above-defined ligands are useful, with the phosphines being particularly preferred.

In a more particular embodiment, preferred ligands useful in this invention are mono-phosphine ligands that are characterized by the general formula:

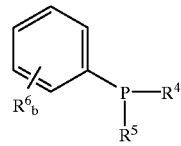

(V)

wherein each $R^4$ and $R^5$ is independently selected from the group consisting of hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.); and $R^6$ is selected from the group consisting of hydrido, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.), silyl, boryl, phosphino, amino, thio, seleno, and combinations thereof; and b is 0, 1, 2, 3, 4 or 5. Optionally two or more $R^6$ groups are joined together in a ring structure. Specific preferred embodiments of $R^6$ are alkyl, substituted alkyl, aryl, substituted aryl, heteroatom-containing alkyl, substituted heteroatom-containing alkyl, heteroatom-containing aryl, and substituted heteroatom-containing aryl.

In an alternative embodiment, the phosphine ligands useful in this invention have a cyclopentadienyl ring, and may be characterized by the formula:

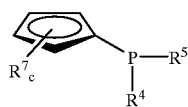

(VI)

where $R^4$ and $R^5$ are defined as above and each $R^7$ is independently selected from the group consisting of hydrido, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.), silyl, boryl, phosphino, amino, thio, seleno, nitro, ester, acid, alkoxy, aryloxy, hydroxy, metallocene, transition metals, COOH, $SO_3G$ (G=Na, K, H, etc.) and combinations thereof; c is 0, 1, 2, 3 or 4 and $R^7$ can occupy any available site on the cyclopentadienyl ring, including an eta-bond (such as an $\eta^5$ bond). More specific embodiments of $R^7$ are those where a mono-cyclopentadienyl or bis-cyclopentadienyl metallocene is formed as part of the ligand. Thus, $R^7$ may be a moiety having a metal atom selected from the group consisting of metals from the Periodic Table of Elements, such as Fe, Rh, Mo, Ru, Cr, Zr, Ti, Hf, Co. Specific examples of $R^7$ include FeCp, CrCp and $ZrCpR_2$, where Cp is a substituted or unsubstituted cyclopentadienyl and R is as defined above. In this specific embodiment, it is intended that the bond between the Cp ring in the ligand and $R^7$ is an $\eta^5$ bond.

Specific embodiments of preferred ligand include:

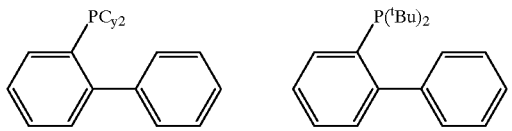

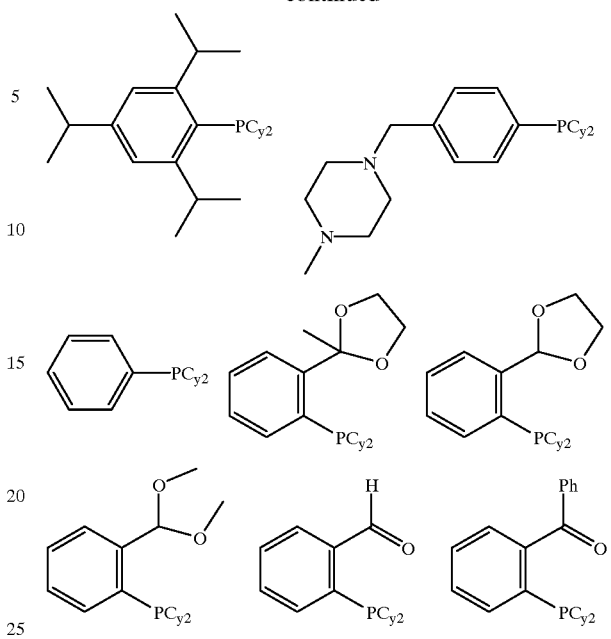

The ligands useful in this invention may be on a support or not. For example, the support could be attached to any one of the R groups. In that embodiment, the support may be a polymer or functionalized polymer, such as polystyrene. In the case of heterogeneous reactions, the ligands may be supported, with or without the metal coordinated (discussed below), on an organic or inorganic support. Suitable supports include silicas, aluminas, zeolites, polyethyleneglycols, polystyrenes, polyesters, polyamides, peptides and the like.

Generally, the ligands useful in this invention may be purchased or prepared using methods known to those of skill in the art. Specific synthesis methods are shown in U.S. patent application Ser. No. 09/062,128, filed Apr. 17, 1998; U.S. patent application Ser. No. 09/296,226, filed Apr. 22, 1999; and U.S. patent application Ser. No. 09/252,182, filed Feb. 18, 1999, each of which are incorporated herein by reference for all purposes. See also, for example, Goetz, H., et al., *Liebigs Ann. Chem.* (1977), No. 4, pp. 556–564.

Metals

The ligand is combined with a metal atom, ion, compound or other metal precursor compound. In many applications, the ligands of this invention will be combined with such a metal compound or precursor and the product of such combination is not determined, if a product forms. For example, the ligand may be added to a reaction vessel at the same time as the metal or metal precursor compound along with the reactants. The metal precursor compounds may be characterized by the general formula $M(L)_n$ (also referred to as $ML_n$ or $M-L_n$) where M is a metal selected from the group consisting of Groups 5, 6, 7, 8, 9 and 10 of the Periodic Table of Elements. In more specific embodiments, M is selected from the group consisting of Ni, Pd, Fe, Pt, Ru, Rh, and Co. L is a ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof. When L is a charged ligand, L is selected from the group consisting of hydrido, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.), silyl, boryl, phosphino, amino, thio, seleno, alkoxy, aryloxy, and combinations thereof. When L is a neutral ligand, L is selected from the group consisting of carbon monoxide, isocyanide, nitrous oxide, $PA_3$, $NA_3$, $OA_2$, $SA_2$, $SeA_2$, and combinations thereof, wherein each A is independently selected from a group consisting of hydrido, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.) and substituted heteroatom-containing hydrocarbyl (e.g., substituted heteroatom-containing alkyl, alkenyl, alkynyl, aryl, aralkyl, alkaryl, etc.), silyl, amino, and combinations thereof. Specific examples of suitable metal precursor compounds include $Pd(dba)_2$ (where dba=dibenzylydieneacteone), $Pd_2(dba)_3$, $Pd(OAc)_2$ (where Ac=acetate), $PdCl_2$, $Pd(TFA)_2$ (where TFA=trifluoroacetate) and the like. In this context, the ligand to metal precursor compound ratio is in the range of about 0.01:1 to about 100:1, more preferably in the range of about 0.5:1 to about 20:1. The metal atom, ion or metal precursor may be supported or not. Supports may be organic or inorganic. Similar to the ligands, the support may be a L. In other embodiments, the support will not form part of the metal precursor and suitable supports include silicas, aluminas, zeolites, polyethyleneglycols, polystyrenes, polyesters, polyamides, peptides and the like. Specific examples of Pd supported metals include Pd/C, $Pd/SiO_2$, $Pd/CaCO_3$, $Pd/BaCO_3$, Pd/aluminate, Pd/aluminum oxide, Pd/polystyrene, although any of the metals listed above could replace Pd in this list, e.g., Ni/C, etc.

In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst.

Solvents

Solvents suitable for the process of the invention are, for example, ethers (e.g., diethyl ether, dimethoxymethane, diethylene glycol, dimethyl ether, tetrahydrofuran (THF), dioxane, diisopropyl ether, tert-butyl methyl ether), hydrocarbons (e.g., hexane, iso-hexane, heptane, cyclohexane, benzene, toluene, xylene), certain alcohols (e.g., tert-butanol), ketones (e.g., acetone, ethyl methyl ketone, iso-butyl methyl ketone), amides (e.g., dimethylformamide, dimethylacetamide, N-methylpyrrolidone), nitriles (e.g., acetonitrile, propionitrile, butyronitrile), water and mixtures thereof. Particularly preferred solvents are ethers (e.g., dioxane, THF), hydrocarbons (e.g., cyclohexane, benzene, toluene, xylene), water and combinations thereof. Most particularly preferred are benzene, toluene, xylene, dioxane, THF, water and combinations thereof. Optionally, the reaction may be conducted using the starting alcohol as the solvent, without additional solvent added.

Bases

Bases which are useful in the process of the invention are alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, alkali metal and alkaline earth metal phosphates, tertiary amines, alkali metal and alkaline earth fluorides, and ammonium fluorides. Particularly preferred are alkali metal and alkaline earth metal phosphates, alkali metal and alkaline earth metal carbonates, alkali metal hydrogen carbonates, alkali metal and alkaline earth fluorides. Most particularly preferred are alkali metal phosphates, alkali metal and alkaline earth metal carbonates, alkali metal and alkaline earth metal alkoxides, and alkali metal and alkaline earth metal hydroxides (such as potassium phosphate and potassium carbonate). The base is preferably used in the process of the invention in an amount of from about 1 to about 1000 mol %, particularly preferably from about 50 to about 500 mol %, very particularly preferably from about 100 to about 400 mol %, in particular from about 150 to about 300 mol %, based on the starting alcohol substrate.

Processes

The process of this invention is a method to convert an alcohol to the corresponding ketone or aldehyde. This process is accomplished by following the reaction outlined generally in Scheme 1, above.

The metal portion of the catalyst (metal precursor or metal complex) is used in the process of this invention in a proportion of from about 0.000001 to about 10 mol %, preferably from about 0.01 to about 5 mol %, particularly preferably from about 0.5 to about 3 mol %, most particularly preferably from about 1.0 to about 1.5 mol %, based on the starting alcohol substrate. The ligand is used in the process in a proportion of from about 0.0000001 to about 40 mol %, preferably from about 0.03 to about 1 mol %, particularly preferably from about 1.5 to about 10 mol %, most particularly preferably from about 1 to about 6 mol %, based on the starting alcohol substrate.

To carry out the process of this invention, the alcohol substrate, the aryl-chloride, a base, a catalytic amount of metal precursor and a catalytic amount of the ligand are added to an inert solvent or inert solvent mixture. In a batch methodology, this mixture is stirred at a temperature of from 0° C. to 200° C., preferably at from 30° C. to 170° C., particularly preferably at from 50° C. to 150° C., most particularly preferably at from 60° C. to 120° C., for a period of from 5 minutes to 100 hours, preferably from 15 minutes to 70 hours, particularly preferably from ½ hour to 50 hours, most particularly preferably from 1 hour to 30 hours. The crude product is freed of the solvent or the solvents and is subsequently purified by methods known to those skilled in the art and matched to the respective product, e.g. by recrystallization, distillation, sublimation, zone melting, melt crystallization or chromatography. The by-product aryl is similarly separated from the desired ketone or aldehyde.

The processes of this invention are particularly effective in performing the above-disclosed chemical transformations. Turn over numbers (TON), which are calculated as the moles of desired product divided by the moles of metal precursor, are typically between about 500 and 100,000. In other embodiments TON's are at least about 50, preferably at least 100, and more preferably at least 200, but can range to at least 500 or even at least 1000. Turn over frequency (TOF), which is calculated as the TON divided by the reaction time in hours, are typically at least about 5, preferably at least 10, more preferably at least 20, and more preferably at least 50, but can range to at least 100 or even at least 200. Selectivity for the reaction to produce the desired product (as compared to undesired side products) are also in the range of from at least 80% to approaching 100%, with selectivity in the range of from about 90% to about 99% being common. Selectivity is calculated as 100 times units of desired product divided by the sum of the units of desired product plus the units of undesired product. The yield from the processes of this invention are typically greater than 90%.

Without wishing to be bound by any particular theory or mechanism, it is believed that the aryl chloride acts as an oxidant in the mechanism, as shown in the following Scheme 2:

Scheme 2

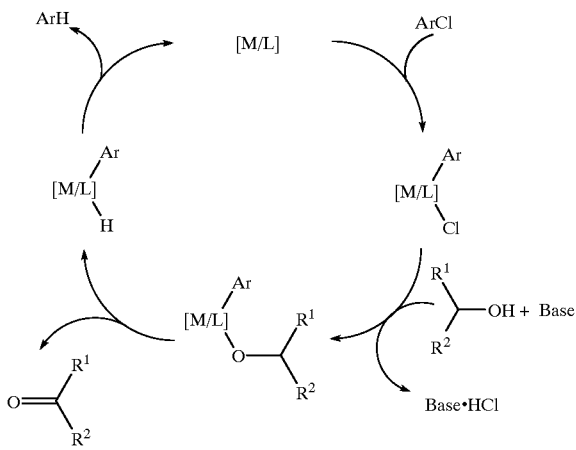

All of the starting materials are added to the processes at one time. Also in Scheme 2, M/L is used to represent the metal/ligand composition or complex (e.g., not the metal precursor only); "Ar" refers to the aryl portion of the aryl chloride material, as defined above more specifically; and $R^1$ and $R^2$ are as defined above. More specifically discussing Scheme 2, it is proposed that the ligand/metal composition or complex begins at the top, shown with [M/L] to indicate the composition or complex as discussed above. The aryl chloride oxidatively adds forming a complex that reacts with the starting alcohol substrate, which, essentially, has been deprotonated by the base. It is proposed that by beta hydride elimination, the product ketone or aldehyde is dissociated from the metal. The reduced aryl chloride (e.g., benzene or benzene derivative) also dissociates from the metal/ligand composition or complex. Thus, those of skill in the art will appreciate that the metal (e.g., metal precursor), ligand, aryl chloride and alcohol substrates may be chosen to avoid ether formation and allow for ketone or aldehyde formation. Also, as discussed above, milder bases may offer superior results.

Products of the process of the invention are the ketones or aldehydes that correspond to the starting alcohols. These products are suitable as precursors for pharmaceuticals, cosmetics, fungicides, herbicides, insecticides, dyes, detergents and polymers, including additives for the same. The other product is the chlorine-abstracted aryl chloride starting material that may act like a solvent, which is typically separated from the ketone or aldehyde by techniques known to those of skill in the art for the removal of solvents (such as distillation, evaporation, etc.).

In another embodiment of this invention, the reaction of this invention can be used to convert a racemic alcohol into an enantiomerically pure or enriched alcohol by the enantioselective oxidation of one enantiomer of the racemic mixture alcohol to the corresponding ketone or aldehyde. This process can be characterized by the following Scheme 3:

Scheme 3

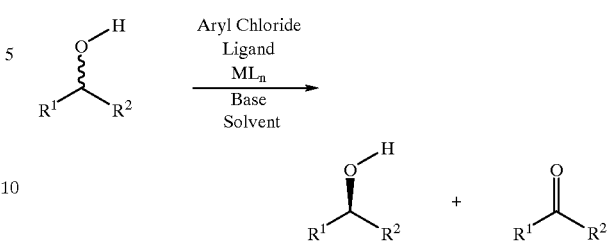

In this embodiment of the invention, the reaction may be run once to achieve a theoretical yield of about 50%. Additionally, the reaction may be run repeated times to achieve a yield of enantiomerically pure alcohol. In this embodiment, it is preferred that the ligand is a chiral ligand.

EXAMPLES

General: All reactions were performed under argon atmosphere in oven-dried glass Schlenk tubes using standard Schlenk techniques. All alcohols, bases ($K_2CO_3$, $K_3PO_4$, NaO$^t$Bu), chlorobenzene (PhCl), bis(dibenzylideneacetone) palladium, diethyl ether, toluene were purchased from commercial sources and used as received. All solvents were of the anhydrous, sure-seal grade. The detailed procedure described for the synthesis and isolation of compound A was generally followed for all Pd/Ligand-catalyzed alcohol oxidation reactions using chlorobenzene. All reactions were performed until complete consumption of the starting alcohols; but the reaction times and conditions have not been minimized. Column chromatography was performed using commercially available Silica Gel 60 (particle size: 0.063–0.100 mm), hexanes and ethyl acetate. Details and results are summarized in Table 1. Ligand 1 has the structure

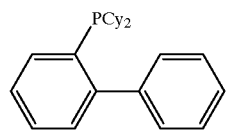

and can be purchased from Strem Chemical. Ligand 2 has the structure

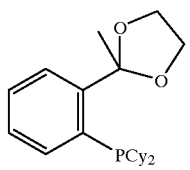

and is prepared as described in U.S. patent application 09/252,182, filed Feb. 18, 1999, and incorporated herein by reference (published as WO 00/08032, also incorporated herein by reference).

Example 1

4,4'-Diflourobenzophenone (A)

A schlenk tube containing the mixture of 4,4'-Diflourobenzhydrol (220 mg, 1.0 mmol), $K_2CO_3$ (276 mg, 2.0 mmol), Pd(dba)$_2$ (6 mg, 10 μmol) and ligand 1 (10 mg, 30 μmol) was degassed thoroughly under vacuum and purged with Ar. Chlorobenzene (0.15 mL) and toluene (4 mL) were added to the schlenk. The mixture was heated at 105° C. for 12 h. The reaction was taken up in ether (100 mL) and washed with $H_2O$ (30 mL) and brine (30 mL). The organic phase was dried over $MgSO_4$, filtered and concentrated under vacuum. The crude product was purified by column chromatography on silica gel using hexanes/ethyl acetate as elute to afford compound A as an off-white solid (215 mg, 98%) after drying under vacuum.

Example 2

Acetophenone (B)

Following the procedure in Example 1, compound B was obtained as an oil (82 mg, 68%) from the reaction of sec-phenethyl alcohol (0.12 mL, 1.0 mmol), chlorobenzene (0.15 mL), $K_2CO_3$ (276 mg, 2.0 mmol), $Pd(dba)_2$ (6 mg, 10 μmol) and ligand 1 (10 mg, 30 μmol) in toluene at 80 ° C. for 24 h.

Example 3

2-Naphthaldehyde (C)

Following the procedure in Example 1, compound C was obtained as a yellowish solid (149 mg, 96%) from the reaction of 2-naphthalenemethanol (158 mg, 1.0 mmol), chlorobenzene (0.15 mL), $K_2CO_3$ (276 mg, 2.0 mmol), $Pd(dba)_2$ (6 mg, 10 μmol) and ligand 1 (10 mg, 30 μmol) in toluene at 105 ° C. for 6 h.

Example 4

Piperonal (D)

Following the procedure in Example 1, compound D was obtained as a pale yellow solid (138 mg, 92%) from the reaction of piperonyl alcohol (152 mg, 1.0 mmol), chlorobenzene (0.15 mL), $K_3PO_4$ (425 mg, 2.0 mmol), $Pd(dba)_2$ (6 mg, 10 μmol) and ligand 1 (10 mg, 30 μmol) in toluene at 105° C. for 14 h.

Example 5

9-Fluorenone (E)

Following the procedure in Example 1, compound E as obtained as yellow solid (179 mg, 100%) from the reaction of 9-hydroxyfluorene (182 g, 1.0 mmol), chlorobenzene (0.15 mL), $K_2CO_3$ (284 mg, 2.0 mmol), $Pd(dba)_2$ (6 mg, 10 μmol) and ligand 2 (11 mg, 31 μmol) in toluene at 105° C. for 12 h.

Example 6

9-Anthraldehyde (F)

Following the procedure in Example 1, compound F was formed (100% GC yield) from the reaction of 9-anthracenemethanol (208 mg, 1.0 mmol), chlorobenzene (0.15 mL), $K_2CO_3$ (276 mg, 2.0 mmol), $Pd(dba)_2$ (6 mg, 10 μmol) and ligand 1 (10 mg, 30 μmol) in toluene at 105° C. for 24 h.

Example 7 p-Methylthiobenzyaldehyde (G)

Following the procedure in Example 1, compound G was obtained as a yellow oil (125 mg, 82%) from the reaction of p-methylthiobenzyl alcohol (154 mg, 1.0 mmol), chlorobenzene (0.15 mL), $K_3PO_4$ (425 mg, 2.0 mmol), $Pd(dba)_2$ (6 mg, 10 μmol) and ligand 1 (10 mg, 30 μmol) in o-xylene at 130° C. for 4 h.

Example 8

Dibenzosuberone (H)

Following the procedure in Example 1, compound H was obtained as a yellow oil (197 mg, 95%) from the reaction of dibenzosuberol (210 mg, 1.0 mmol), chlorobenzene (0.15 mL), $K_2CO_3$ (276 mg, 2.0 mmol), $Pd(dba)_2$ (6 mg, 10 μmol) and ligand 1 (10 mg, 30 μmol) in toluene at 105° C. for 48 h.

Example 9 trans-4-Stilbenecarboxaldehyde (I)

Following the procedure in Example 1, compound I was obtained as an off-white solid (196 mg, 94%) from the reaction of trans-stilbenemethanol (210 mg, 1.0 mmol), chlorobenzene (0.15 mL, 1.5 mmol), $K_3PO_4$ (425 mg, 2.0 mmol), $Pd(dba)_2$ (6 mg, 10 μmol) and ligand 1 (10 mg, 30 μmol) in toluene at 110° C. for 14 h.

Example 10

4,4'-Bis(dimethyamino)benzophenone (J)

Following the procedure in Example 1, compound J was obtained as an off-white solid (255 mg, 95%) from the reaction of 4,4'-Bis(dimethyamino)benzhydrol (270 mg, 1.0 mmol), chlorobenzene (0.15 mL, 1.5 mmol), $K_3PO_4$ (425 mg, 2.0 mmol), $Pd(dba)_2$ (6 mg, 10 μmol) and ligand 1 (10 mg, 30 μmol) in toluene at 110° C. for 18 h.

Example 11

Dibenz(C,E)oxepin-5(7H)-one (K)

Following the procedure in Example 1, compound K was obtained as an off-white solid (202 mg, 96%) from the reaction of 2,2'-biphenyldimethanol (214 mg, 1.0 mmol), chlorobenzene (0.15 mL), $K_2CO_3$ (276 mg, 2.0 mmol), $Pd(dba)_2$ (6 mg, 10 μmol) and ligand 1 (10 mg, 30 μmol) in toluene at 105° C. for 11.5 h.

Example 12

1,5-Dimethyl-bicyclo-[3,2,1]-octane-8-on (L)

Following the procedure in Example 1, compound L was formed (100% GC yield) from the reaction of 1,5-dimethyl-bicyclo-[3,2,1]-octane-8-ol (154 mg, 1.0 mmol), chlorobenzene (0.10 mL, 1.0 mmoL), NaO$^t$Bu (192 mg, 2.0 mmol), $Pd(dba)_2$ (0.29 mg, 0.5 μmol) and ligand 1 (0.53 mg, 1.5 μmol) in toluene at 105° C. for 2 h.

Example 13

(1S)-(−)-Camphor (M)

Following the procedure in Example 1, compound M was formed (100% GC yield) from the reaction of [(1S)-endo]-(−)-borneol (171 mg, 1.1 mmol), chlorobenzene (0.11 mL, 1.1 mmoL), NaO$^t$Bu (192 mg, 2.0 mmol), $Pd(dba)_2$ (1.15 mg, 2.0 μmol) and ligand 1 (2.1 mg, 6.0 μmol) in toluene at 105° C. for 2 h.

TABLE 1

| Ex. | Alcohol | Base | Temp. (° C.) | Entry | Product | Yield (%) |
|---|---|---|---|---|---|---|
| 1 | (4-F-C6H4)2CH(OH) | $K_2CO_3$ | 105 | A | (4-F-C6H4)2C=O | 98 |
| 2 | 1-phenylethanol | $K_2CO_3$ | 80 | B | acetophenone | 68 |
| 3 | 2-naphthalenemethanol | $K_2CO_3$ | 105 | C | 2-naphthaldehyde | 96 |
| 4 | piperonyl alcohol | $K_3PO_4$ | 105 | D | piperonal | 92 |
| 5 | 9-fluorenol | $K_2CO_3$ | 105 | E | 9-fluorenone | 92 |
| 6 | 9-anthracenemethanol | $K_2CO_3$ | 105 | F | 9-anthraldehyde | 100, GC |
| 7 | 4-(methylthio)benzyl alcohol | $K_3PO_4$ | 130 | G | 4-(methylthio)benzaldehyde | 82 |
| 8 | 10,11-dihydro-5H-dibenzo[a,d]cyclohepten-5-ol | $K_2CO_3$ | 100 | H | 10,11-dihydro-5H-dibenzo[a,d]cyclohepten-5-one | 95 |
| 9 | 4-styrylbenzyl alcohol | $K_3PO_4$ | 110 | I | 4-styrylbenzaldehyde | 94 |

TABLE 1-continued

| Ex. | Alcohol | Base | Temp. (° C.) | Entry | Product | Yield (%) |
|---|---|---|---|---|---|---|
| 10 | Me₂N–C₆H₄–CH(OH)–C₆H₄–NMe₂ | K₃PO₄ | 10 | J | Me₂N–C₆H₄–C(O)–C₆H₄–NMe₂ | 95 |
| 11 | 2,2'-bis(hydroxymethyl)biphenyl | K₂CO₃ | 105 | K | dibenz[c,e]oxepin-5(7H)-one | 96 |
| 12 | isopinocampheol (HO-) | NaO$^t$Bu | 105 | L | isopinocamphone | 100, GC |
| 13 | isopinocampheol (-OH) | NaO$^t$Bu | 105 | M | isopinocamphone | 100, GC |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A process for oxidizing an alcohol to its corresponding aldehyde or ketone comprising, reacting said alcohol, aryl chloride, ligand, metal in the presence of a base; wherein said ligand is selected from the group consisting of $PR_3$, $NR_3$, $OR_2$ or $:CR_2$, wherein each R is independently selected from the group consisting of hydrocarbyl, substituted hydrocarbyl, heteroatom-containing hydrocarbyl and substituted heteroatom-containing hydrocarbyl, and wherein said ligand comprises at least one alkyl or substituted alkyl.

2. The process of claim 1, wherein each R is independently selected from the group consisting of alkyl, substituted alkyl, aryl, substituted aryl and combinations thereof.

3. The process of claim 1, wherein said aryl chloride is characterized by the general formula:

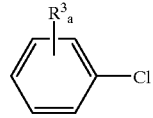

where $R^3$ is selected from the group consisting of hydrido, hydrocarbyl, substituted hydrocarbyl, heteroatom-containing hydrocarbyl, substituted heteroatom-containing hydrocarbyl, silyl, boryl, phosphino, amino, thio, seleno, and combinations thereof and a is 0, 1, 2, 3, 4 or 5; and optionally two or more $R^3$ groups are joined together in a ring structure.

4. The process of claim 3, wherein a is 0.

5. The process of claim 1, wherein said ligand that is characterized by the general formula:

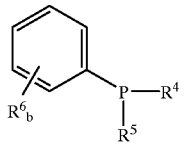

wherein each $R^4$ and $R^5$ is independently selected from the group consisting of alkyl and substituted alkyl; and $R^6$ is selected from the group consisting of hydrido, hydrocarbyl, substituted hydrocarbyl, heteroatom-containing hydrocarbyl and substituted heteroatom-containing hydrocarbyl, silyl, boryl, phosphino, amino, thio, seleno, and combinations thereof; and b is 0, 1, 2, 3, 4 or 5; and optionally two or more $R^6$ groups are joined together in a ring structure.

6. The process of claim 5, wherein each $R^4$ and $R^5$ is cyclohexyl or tert-butyl.

7. The process of claim 1, wherein said metal is in the form of a metal precursor that is characterized by the formula $M(L)_n$ where M is a metal selected from the group consisting of Groups 5, 6, 7, 8, 9 and 10 of the Periodic Table of Elements; L is an anionic or neutral compound and n is an integer greater than 0.

8. The process of claim 7, wherein M is selected from the group consisting of Ni, Pd, Fe, Pt, Ru, Rh, Ir and Co.

9. The process of claim 8, wherein M is selected from the group consisting of Ni or Pd.

10. The process of claim 7, wherein L is selected from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof.

11. The process of claim 1, wherein said alcohol is represented by the general formula: $R^1R^2CHOH$, where $R^1$ is selected from the group consisting of hydrido, hydroxyl, sulfhydryl, amino, substituted amino, hydrocarbyl, substituted hydrocarbyl, heteroatom-containing hydrocarbyl, substituted heteroatom-containing hydrocarbyl, silyl, cyano, boryl, thio and phosphino; and $R^2$ is selected from the group consisting of aryl, substituted aryl, heteroatom-containing aryl and substituted heteroatom-containing aryl.

12. The process of claim 1, wherein said alcohol is represented by the general formula:

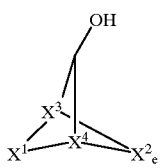

where $X^1$, $X_2^e$, $X^3$ and $X^4$ are independently a moiety that contains up to 50 atoms and e is 0 or 1.

13. A process characterized by the following scheme:

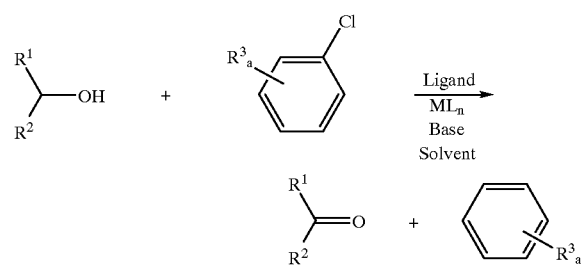

wherein $R^1$ is selected from the group consisting of hydrido, hydroxyl, sulfhydryl, amino, substituted amino, hydrocarbyl, substituted hydrocarbyl, heteroatom-containing hydrocarbyl, substituted heteroatom-containing hydrocarbyl, silyl, cyano, boryl, thio and phosphino; $R^2$ is selected from the group consisting of aryl, substituted aryl, heteroatom-containing aryl and substituted heteroatom-containing aryl; $R^3$ is selected from the group consisting of hydrido, hydrocarbyl, substituted hydrocarbyl, heteroatom-containing hydrocarbyl, substituted heteroatom-containing hydrocarbyl, silyl, boryl, phosphino, amino, thio, seleno, and combinations thereof and a is 0, 1, 2, 3, 4 or 5; and optionally two or more $R^3$ groups are joined together in a ring structure; Ligand is selected from the group consisting of $PR_3$, $NR_3$, $OR_2$ or $:CR_2$ wherein each R is independently selected from the group consisting of hydrocarbyl, substituted hydrocarbyl, heteroatom-containing hydrocarbyl and substituted heteroatom-containing hydrocarbyl and wherein said Ligand comprises at least one alkyl or substituted alkyl; $M(L)_n$ is where M is a metal selected from the group consisting of Groups 5, 6, 7, 8, 9 and 10 of the Periodic Table of Elements, L is an anionic or neutral compound and n is an integer greater than 0; Base is a base selected from the group consisting of organic and inorganic bases; and Solvent is a solvent selected from the group consisting of coordinating and non-coordinating solvents.

14. A process for converting a cyclic or bicyclic aliphatic alcohol to its corresponding ketone or aldehyde comprising reacting said alcohol with an aryl chloride oxidant in the presence of base and either (1) metal and ligand composition or (2) metal/ligand complex, wherein said ligand is selected from the group consisting of $PR_3$, $NR_3$, $OR_2$ or $:CR_2$, wherein each R is independently selected from the group consisting of hydrocarbyl, substituted hydrocarbyl, heteroatom-containing hydrocarbyl and substituted heteroatom-containing hydrocarbyl, and wherein said ligand comprises at least one alkyl or substituted alkyl; and wherein said alcohol is represented by the general formula:

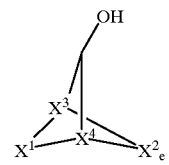

where $X^1$, $X_2^e$, $X^3$ and $X^4$ are independently a moiety that contains up to 50 atoms and e is 0 or 1.

15. A process for converting an aromatic aliphatic alcohol to its corresponding ketone or aldehyde comprising reacting said alcohol with an aryl chloride oxidant in the presence of base and either (1) metal and ligand composition or (2) metal/ligand complex, wherein said ligand is selected from the group consisting of $PR_3$, $NR_3$, $OR_2$ or $:CR_2$, wherein each R is independently selected from the group consisting of hydrocarbyl, substituted hydrocarbyl, heteroatom-containing hydrocarbyl and substituted heteroatom-containing hydrocarbyl, and wherein said ligand comprises at least one alkyl or substituted alkyl; and wherein said alcohol is represented by the general formula: $R^1R^2CHOH$, where $R^1$ is selected from the group consisting of hydrido, hydroxyl, sulfhydryl, amino, substituted amino, hydrocarbyl, substituted hydrocarbyl, heteroatom-containing hydrocarbyl, substituted heteroatom-containing hydrocarbyl, silyl, cyano, boryl, thio and phosphino; and $R^2$ is selected from the group consisting of aryl, substituted aryl, heteroatom-containing aryl and substituted heteroatom-containing aryl.

16. The process of claim 15, wherein said ligand in said composition or complex is represented by the general formula $PR^3$ wherein each R is independently selected from the group consisting of hydrocarbyl, substituted hydrocarbyl, heteroatom-containing hydrocarbyl and substituted heteroatom-containing hydrocarbyl, and wherein said ligand comprises at least one alkyl or substituted alkyl.

17. The process of claim 16, wherein said aryl chloride is chlorobenzene.

18. A process for enantioselective oxidation of a racemic alcohol comprising (1) reacting said racemic alcohol, aryl chloride, ligand, and metal in the presence of a solvent and base; and (2) forming a mixture comprising one enantiomer of said racemic alcohol and the corresponding ketone or aldehyde of said alcohol from the second of enantiomer of said racemic alcohol; wherein said ligand is selected from the group consisting of $PR_3$, $NR_3$, $OR_2$ or $:CR_2$, wherein each R is independently selected from the group consisting of hydrocarbyl, substituted hydrocarbyl, heteroatom-containing hydrocarbyl and substituted heteroatom-containing hydrocarbyl, and wherein said ligand comprises at least one alkyl or substituted alkyl.

19. The process of claim 18, further comprising hydrogenation of the reaction mixture and then continuing or repeating the reacting step so as to further enrich the enantiomeric excess of the desired enantiopure alcohol.

20. The process of claim 17, wherein said ligand is chiral.

* * * * *

UNITED STATES PATENT AND TRADEMARK OFFICE
CERTIFICATE OF CORRECTION

PATENT NO. : 6,350,916
DATED : February 26, 2002
INVENTOR(S) : Guram, Anil et al.

It is certified that error appears in the above-identified patent and that said Letters Patent is hereby corrected as shown below:

Column 23,
Line 42, "$X_2^e$" should be replaced with -- $X_e^2$ --

Column 24,
Line 36, "$X_2^e$" should be replaced with -- $X_e^2$ --

Signed and Sealed this

Twenty-first Day of May, 2002

Attest:

Attesting Officer

JAMES E. ROGAN
Director of the United States Patent and Trademark Office